(12) United States Patent
Kamata et al.

(10) Patent No.: US 8,535,510 B2
(45) Date of Patent: Sep. 17, 2013

(54) METHOD FOR MEASURING SUBSTRATE CONCENTRATION AND APPARATUS FOR MEASURING SUBSTRATE CONCENTRATION

(75) Inventors: Tatsuo Kamata, Kyoto (JP); Takeshi Takagi, Kyoto (JP); Yuki Ito, Kyoto (JP)

(73) Assignee: Arkray, Inc., Kyoto (JP)

( * ) Notice: Subject to any disclaimer, the term of this patent is extended or adjusted under 35 U.S.C. 154(b) by 371 days.

(21) Appl. No.: 12/450,775

(22) PCT Filed: Apr. 15, 2008

(86) PCT No.: PCT/JP2008/057366
§ 371 (c)(1),
(2), (4) Date: Jul. 30, 2010

(87) PCT Pub. No.: WO2008/133121
PCT Pub. Date: Nov. 6, 2008

(65) Prior Publication Data
US 2010/0288650 A1 Nov. 18, 2010

(30) Foreign Application Priority Data
Apr. 17, 2007 (JP) .................................. 2007-108630

(51) Int. Cl.
*G01N 27/327* (2006.01)
(52) U.S. Cl.
USPC ................................... 205/777.5; 204/403.14
(58) Field of Classification Search
USPC .... 204/403.01–403.15, 409–412; 205/777.5, 205/778, 792
See application file for complete search history.

(56) References Cited

U.S. PATENT DOCUMENTS

| 4,407,959 | A | * | 10/1983 | Tsuji et al. | ................. | 204/403.1 |
| 4,587,219 | A |   | 5/1986  | Claren et al. | | |
| 2004/0259264 | A1 | | 12/2004 | Morita et al. | | |
| 2005/0089944 | A1 | | 4/2005  | Shieh et al. | | |

FOREIGN PATENT DOCUMENTS

| JP | 57-088265 A | 6/1982 |
| JP | 63-259457 A | 10/1988 |
| JP | 64-065441 A | 10/1989 |
| JP | 03-111753 A | 5/1991 |

(Continued)

OTHER PUBLICATIONS

Dock et al. "Multivariate data analysis of dynamic amperometric biosensor responses from binary analyte mixtures—application of sensitivity correction algorithms," Talanta 65 (2005) 298-305.*

(Continued)

*Primary Examiner* — Alex Noguerola
(74) *Attorney, Agent, or Firm* — Rader, Fishman & Grauer PLLC

(57) ABSTRACT

This invention provides a substrate concentration measuring method for measuring a concentration of a substrate included in a specimen based on an output for measurement from an enzyme electrode when the enzyme electrode and the substrate are reacted with each other, the substrate concentration is calculated using an output for correction from the enzyme electrode obtained when a reference solution whose substrate concentration is known and the enzyme electrode are reacted with each other before or after the enzyme electrode and the substrate are reacted with each other. For example, the output for correction is measured by each specimen. In this method, the substrate concentration may be calculated using the output for correction for the specimen to be measured and an output for correction corresponding to the at least one other specimen and measured prior to the output for correction.

11 Claims, 5 Drawing Sheets

(56) References Cited

FOREIGN PATENT DOCUMENTS

| | | |
|---|---|---|
| JP | 08-136498 A | 5/1996 |
| JP | 3723827 B2 | 12/2005 |
| WO | WO-03/036285 A1 | 5/2003 |

OTHER PUBLICATIONS

Haugen et al., "A calibration method for handling the temporal drift of solid state gas-sensors," Analytica Chimica Acta 407 (2000) 23-39.*

Cortón et al. "Simple flow injection analysis system for determination of added sugars in dairy products," Journal of Diary Research (1998) 65 675-680.*

International Search Report, 4 sheets, Jun. 7, 2008.

EPO Search Report, 10 sheets, May 7, 2010.

English language translation of the Japanese Office Action issued Aug. 30, 2011 for corresponding Japanese Application No. 2009-511814.

* cited by examiner

METHOD FOR MEASURING SUBSTRATE CONCENTRATION AND APPARATUS FOR MEASURING SUBSTRATE CONCENTRATION

BACKGROUND OF THE INVENTION

1. Technical Field

The present invention relates to a method and a device for carrying out the measurement of a substrate such as glucose included in a specimen.

2. Background Art

There is a conventionally known method called an electrode method, which is a method for measuring a concentration of a substrate such as glucose. According to the method, information correlating with a substrate concentration in a specimen is outputted to an electrode in contact with the specimen, and the substrate concentration is calculated based on the output. An enzyme electrode is conventionally used as the electrode. A conventionally known example of the enzyme electrode has a structure where an enzyme-immobilized film and a substrate selectively permeable film are multilayered on a surface of the electrode.

An enzyme electrode does not have a constant sensitivity. The sensitivity is liable to be degraded depending on environments where it is used, or by a repeated use of the enzyme electrode. The factors causing the degradation of the sensitivity are, for example, alternation of an activity of the enzyme due to temperature changes and deactivation of the enzyme, deterioration of substrate permeability in the substrate selectively permeable film, and oxidization of the electrode surface. The enzyme electrode is thus deteriorated as it is more frequently used and needs to be replaced after being used over a definite period, and calibration is a necessary measure to deal with the sensitivity variation before the replacement of the enzyme electrode.

In an automatic measuring device, for example, the calibration is performed at the startup of the device, and is generally performed at certain time intervals, or per a certain number of measurements in a case where the device is uninterruptedly used over an extended period of time. The sensitivity of the enzyme electrode is variable owing to the various factors described above. In addition to that, the sensitivity may be changeable during the calibration, and it is difficult to predict or grasp what factor causes the sensitivity of the enzyme electrode to change. Therefore, measured values obtained immediately after the calibration can be very reliable, however, it is not necessarily a case that the reliability of measured values obtained between the calibrations is equally high.

In the case of measuring a substrate concentration using an enzyme electrode placed in a flow cell, for example, a base current Rb outputted from the enzyme electrode substantially stays at a constant level as illustrated in FIG. 7A when the sensitivity of the enzyme electrode remains unchanged, and the output from the enzyme electrode is increased when a specimen is introduced. On the contrary, the base output is lowered as illustrated in FIG. 7B under such circumstances that the sensitivity of the enzyme electrode may be degraded.

To calculate the substrate concentration, the output from the enzyme electrode before the supply of the specimen to the enzyme electrode (T1) is sampled as a base output Rb, and the output from the enzyme electrode when a predetermined amount of time passed after the supply of the specimen to the enzyme electrode (T2) is sampled as an output for measurement Re, and a difference between the output for measurement Re and the base output Rb is obtained, so that the substrate concentration is calculated based on the difference. More specifically describing the calculation, the base output when the output for measurement Re is sampled is used as the base output Rb before the output for measurement Re is sampled on the assumption that the base output (sensitivity of the enzyme electrode) is constant.

Therefore, as illustrated in FIG. 7B, a calculated value of the substrate concentration is different to a true value in a case where a base output Rb2 obtained by sampling the output for measurement Re is different to a base output Rb1 previously measured.

When the enzyme electrode deteriorated over time is replaced, the sensitivity of the enzyme electrode shows a sudden drop immediately after the replacement, and is thereafter stabilized to stay at a certain value. Therefore, it is pointless to perform the calibration before the sensitivity of the enzyme electrode is stabilized after the replacement of the enzyme electrode. Thus, the enzyme electrode after the replacement is not ready for measurements until the sensitivity of the enzyme electrode is stabilized and the calibration is completed.

[Patent Document 1] Japanese Patent Application Laid-Open (JP-A) No. 59-082020

[Patent Document 2] Japanese Patent No. 3723827

DISCLOSURE OF THE INVENTION

Problem to be Solved by the Invention

An object of the present invention is to improve a measurement accuracy and reliability in the measurement of a concentration of a substrate such as glucose included in a specimen using an enzyme electrode.

Means for Solving the Problems

A first aspect of the present invention provides a substrate concentration measuring method for measuring a concentration of a substrate included in a specimen based on an output for measurement from an enzyme electrode when the enzyme electrode and the substrate are reacted with each other, wherein the substrate concentration is calculated using an output for correction from the enzyme electrode obtained when a reference solution whose substrate concentration is known and the enzyme electrode are reacted with each other before or after the enzyme electrode and the substrate are reacted with each other.

The output for correction may be measured by each specimen, or the outputs for correction for a certain number of specimens may be correctively measured.

For example, the calculation of a substrate concentration employs a current output for correction for the specimen to be measured, and a preceding output for correction corresponding to at least the one other specimen and measured prior to the current output for correction. In this case, a mean value of the preceding output for correction and the current output for correction may be used to calculate the substrate concentration.

A substrate concentration may be calculated based on a difference between the output for measurement and a base output measured when washing the enzyme electrode. When the substrate concentration is thus calculated, it is preferable to estimate the base output to be subtracted from the output for measurement to obtain the difference based on an estimation curve drawn so as to correspond to a time-dependent variation of a plurality of base outputs when a change that is equal to or greater than a given value is detected between the plurality of base outputs.

An enzyme electrode is placed in, for example, a flow cell. An example of the specimen is whole blood, and an example of the substrate is glucose.

A second aspect of the present invention provides a substrate concentration measuring device including a calculating unit for calculating a concentration of a substrate included in a specimen based on an output for measurement from an enzyme electrode when the enzyme electrode and the substrate are reacted with each other, wherein the calculating unit is configured to calculate a substrate concentration using an output for correction from the enzyme electrode obtained when a reference solution whose substrate concentration is known and the enzyme electrode are reacted with each other before or after the enzyme electrode and the substrate are reacted with each other.

For example, the calculating unit is configured to calculate the substrate concentration using the output for correction measured by each specimen or the outputs for correction correctively measured for a certain number of specimens.

For example, the calculating unit is configured to calculate the substrate concentration using a current output for correction for the specimen to be measured and a preceding output for correction corresponding to the at least one other specimen and measured prior to the current output for correction. In this case, the calculating unit may be configured to calculate the substrate concentration using a mean value of the current output for correction and the preceding output for correction.

The calculating unit may be configured to calculate the substrate concentration based on a difference between the output for measurement and a base output measured when washing the enzyme electrode. When the calculating unit thus calculates the substrate concentration, the calculating unit is preferably configured to calculate the substrate concentration after estimating the base output to be subtracted from the output for measurement to obtain the difference based on an estimation curve drawn so as to correspond to a time-dependent variation of a plurality of base outputs when a change that is equal to or greater than a given value is detected between the plurality of base outputs.

The enzyme electrode is placed in, for example, a flow cell, and an enzyme electrode which selectively reacts with glucose as a substrate is used as the enzyme electrode.

The substrate concentration measuring device according to the present invention preferably further includes: a specimen preparing unit for preparing the specimen to be reacted with the enzyme electrode; a reference solution retaining tank for retaining the reference solution for obtaining the output for correction; and a selecting unit for selecting one of a state where the specimen is to be supplied and a state where the reference solution is to be supplied for the enzyme electrode.

DESCRIPTION OF REFERENCE SYMBOLS

Figure 1:
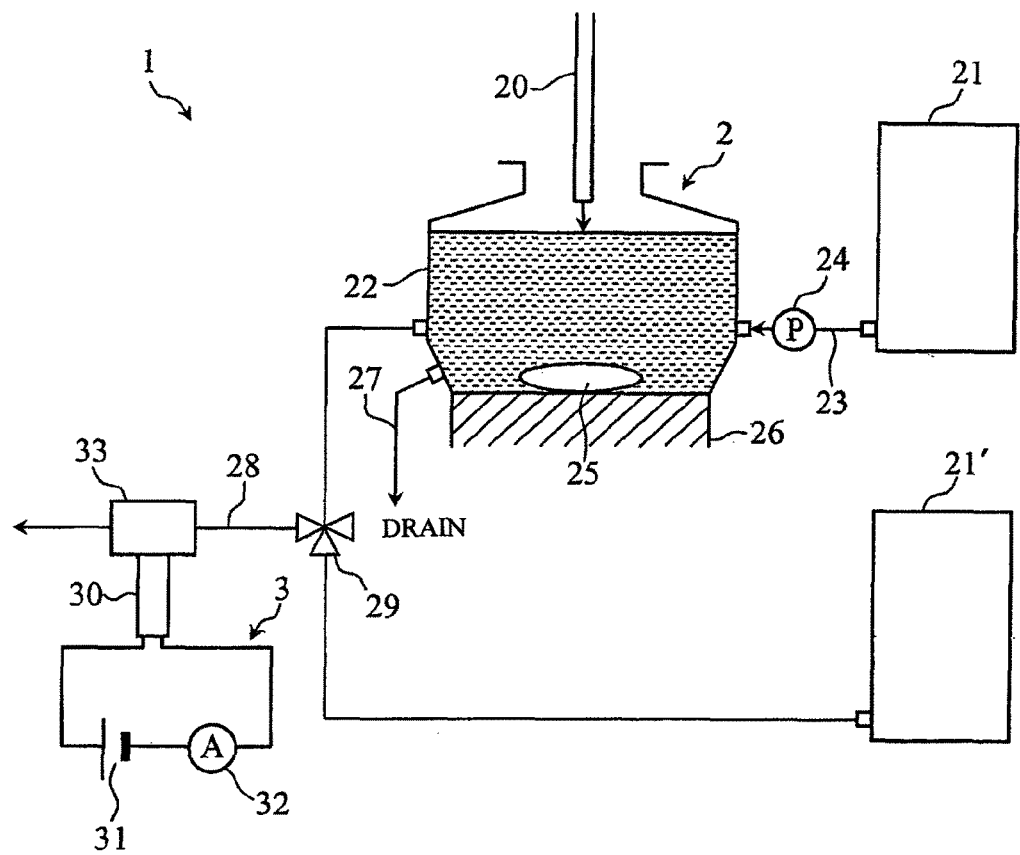
FIG. 1 is a sectional view schematically illustrating a structure of a concentration measuring device according to the present invention.

1: concentration measuring device
2: specimen preparation mechanism (specimen preparation unit)
21': reference solution tank (reference solution containing tank)
29: valve (selecting unit)
33: flow cell
30: enzyme electrode
5: calculating section (calculating unit)

BEST MODE FOR CARRYING OUT THE INVENTION

The present invention is described below referring to the drawings.

A concentration measuring device 1 illustrated in FIG. 1 is configured to measure a specimen adjusted in a specimen preparation mechanism 2 using a measurement mechanism 3.

The specimen preparation mechanism 2 is a mechanism for preparing a specimen from an analyte, and comprises a nozzle 20, a reagent bottle 21, and a preparation tank 22.

The nozzle 20 is a nozzle for supplying an analyte into the preparation tank 22. Examples of the analyte to be used are biochemical specimens such as blood, urine and saliva, or diluents obtained therefrom. In a case where blood is used as the specimen, any of the whole blood and plasma or blood serum can be used.

The reagent bottle 21 retains therein a reagent for diluting an analyte or washing the preparation tank 22. The reagent bottle 21 is connected to the preparation tank 22 via a pipe 23 interposed therebetween. A pump 24 is provided at an intermediate position in the pipe 23, and a configuration is given such that a force generated by the pump 24 serves to supply the reagent retained in the reagent bottle 21 into the preparation tank 22.

An example of the reagent is a buffer solution. The buffer solution is not particularly limited as far as it can adjust the reaction pH of a substrate in a targeted range, and phosphates, for example, can be used. The concentration of the buffer solution in the reagent is set to, for example, 0.0001 to 0.1000 M. The examples of the reagent include, in addition to the buffer solution, conventional hemolytic agents and preservatives such as an azide compound, and the reagent may further include, for example, sodium oxide or potassium oxide.

The preparation tank 22 provides a site where the specimen can be prepared. The preparation tank 22 is configured such that the analyte is supplied from the nozzle 20, and the reagent is supplied from the reagent bottle 21. The preparation tank 22 comprises therein an agitator 25, and when the agitator 25 is rotated by a stirrer 26, the analyte and the reagent are mixed with each other. The preparation tank 22 is connected to a drain pipe 27 for discarding the prepared solution of the preparation tank 22 and further connected to an enzyme electrode 30 of a measurement mechanism 3 by way of a pipe 28. A valve 29 is provided at an intermediate position in the pipe 28, and a reference solution tank 21' is connected to the valve 29. The valve 29 is thereby configured to select one of a state where the specimen prepared in the preparation tank 22, reagent of the reagent bottle 20 or reference solution of the reference solution tank 21' is to be supplied and a state where the above-described specimen, reagent, or reference solution is not to be supplied for the enzyme electrode 30 of the measurement mechanism 3. As the reference solution can be used a reagent whose substrate concentration is known, for example, diluents obtained from any reference solution which is conventionally used in the calibration (diluted 50-200 times).

The measurement mechanism 3 comprises the enzyme electrode 30, a power supply 31 and a current value measuring unit 32.

Figure 2:
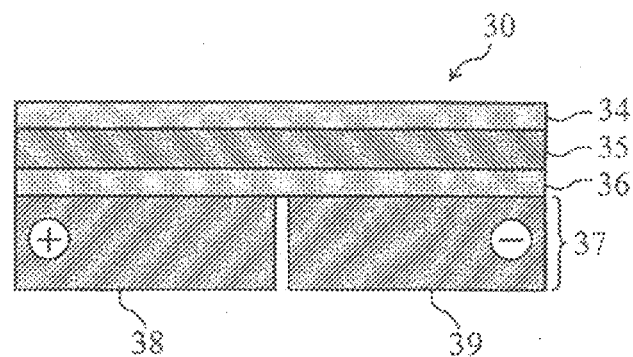
FIG. 2 is a sectional view schematically illustrating a structure of an enzyme electrode provided in the concentration measuring device illustrated in FIG. 1.
Figure 3:
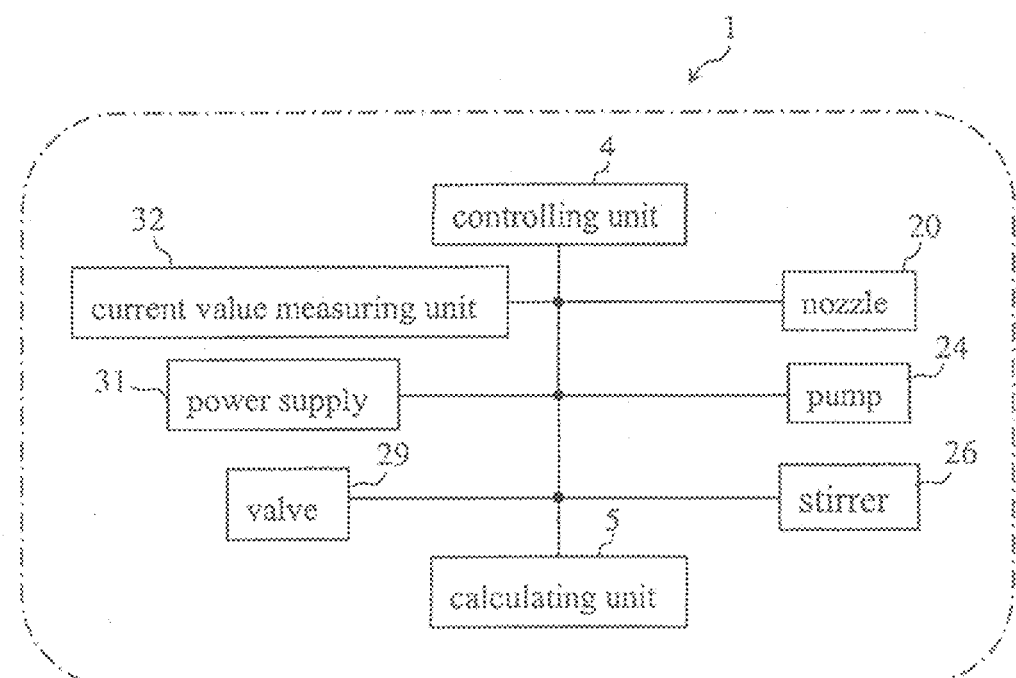
FIG. 3 is a block diagram of the substrate concentration measuring device illustrated in FIG. 1.

The enzyme electrode 30 outputs an electrophysical quantity corresponding to the amount of electrons transferred to and received from a substrate in a specimen. The enzyme electrode 30 is arranged in a flow cell 33, and as illustrated in FIG. 2, the enzyme electrode 30 comprises a first selectively permeable film 34, an enzyme immobilized film 35, a second selectively permeable film 36, and a electrode 37.

The first selective transmission film 34 is a film for selectively supplying a substrate in a specimen to the enzyme immobilized film 35. The first selective transmission film 34 to be used is a various conventionally available film, although being selected depending on the type of a substrate.

The enzyme immobilized film 35 is a film for generating hydrogen peroxide by oxidizing or reducing a substrate, and is configured to include an oxidase. The oxidase used in the present invention is selected depending on the type of a substrate. Examples of the substrate to be measured by the concentration measuring device 1 are glucose and lactate, and glucose oxidase or lactate oxidase can be mentioned as the enzyme.

The second selectively permeable film 36 is provided to selectively supply a reactant such as hydrogen peroxide produced from the substrate by the enzyme to the electrode 37. Usable examples of the second selectively permeable film 36 are acetylcellulose-based and polyallylamine-based films.

The electrode 37 outputs an electrical signal corresponding to the amount of the supplied hydrogen peroxide, in other words, the concentration of the substrate. The electrode 37 to be used is an electrode in which platinum is used as an anode 38, while silver is used as a cathode 39.

The power supply 31 illustrated in FIG. 1 applies a voltage to the enzyme electrode 30 (electrode 37). A direct-current power supply, for example, is used as the power supply 31, and the voltage applied to the enzyme electrode 30 (electrode 37) is set to, for example, 0.1 to 1.0 V.

The current value measuring unit 32 is a unit for measuring the current value when a voltage is applied between the anode 38 and the cathode 39. The current value is intermittently measured by the current value measuring unit 32, and a measurement interval is set to, for example, 50 to 200 msec.

Figure 4:
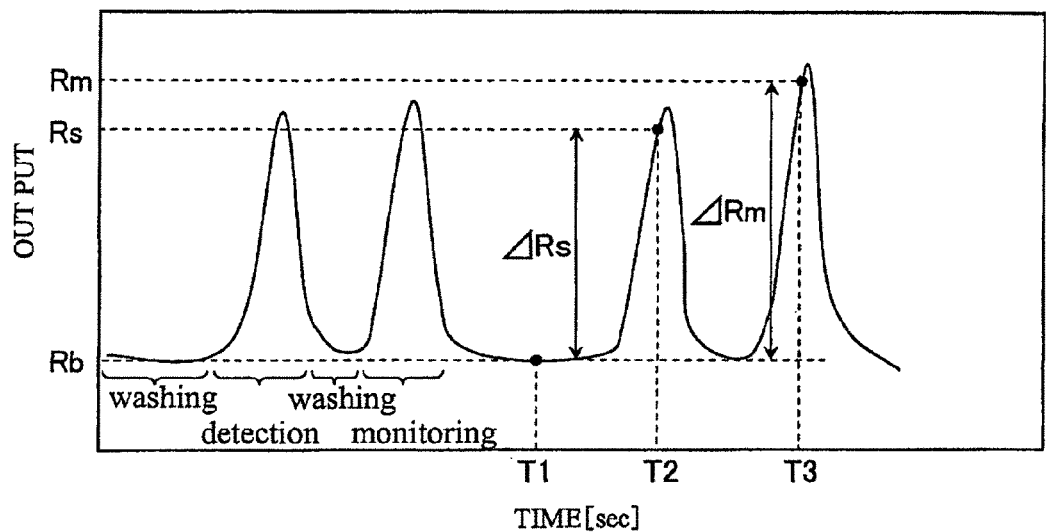
FIG. 4 is a timing chart of outputs from the enzyme electrode provided to describe an example of an operation in a calculating section.

As illustrated in FIG. 4, the substrate concentration measuring device 1 further includes a controlling unit 4 and a calculating unit 5.

The controlling unit 4 controls the operations of the respective structural elements. More specifically, the controlling unit 4 controls the operations of the nozzle 20, pump 24, stirrer 26, valve 29 and the like. The controlling unit 4 further controls the operation of the measurement mechanism 3. More specifically, the controlling unit 4 controls the power supply 31 to thereby select one of a state where a voltage is to be applied to the electrode 37 and a state where the voltage is not to be applied thereto, and controls the current value measuring unit 32 to thereby control a timing of measuring a current value. The measuring operation of the current value measuring unit 31 is controlled by the controlling unit 4 so that the current value is repeatedly measured at the intervals of, for example, 50 to 200 μsec.

The calculating unit 5 is provided to calculate a concentration of a substrate, such as glucose, included in the analyte based on a result of the measurement by the current value measuring unit 32. The calculating unit 5 stores therein programs necessary for the calculation, and the operation of the calculating unit is controlled by the controlling unit 4.

Next, an operation of the substrate concentration measuring device 1 is described.

In the substrate concentration measuring device 1, the specimen, prepared solution, reagent and reference solution are repeatedly supplied to the flow cell 33. More specifically, the substrate concentration measuring device 1 repeatedly carries out: washing the enzyme electrode using the reagent; measuring the substrate using the prepared solution; washing the enzyme electrode using the reagent; and monitoring the sensitivity of the enzyme electrode 30 using the reference solution.

When the enzyme electrode is washed with the reagent, the reagent of the reagent bottle 21 is supplied to the flow cell 33 through the preparation tank 22.

To measure the substrate, the analyte such as whole blood and the reagent are supplied to the preparation tank 22 and mixed therein, and the specimen thereby prepared is supplied to the flow cell 33 so that the output from the enzyme electrode 30 is detected. The analyte is supplied to the preparation tank 22 through the nozzle 20, and an amount of the analyte to be supplied is set to 4 to 20 μL in a case where whole blood is used. The reagent is supplied to the preparation tank 22 through the pump 24, an amount of the reagent to be supplied is set to about 100 times as much as the whole blood. The analyte and the reagent are mixed with each other by rotating the agitating member 25 of the stirrer 26.

In the enzyme electrode 30, the substrate permeates through the first selectively permeable film 34 to be supplied to the enzyme-immobilized film 35. In the enzyme-immobilized film 35, the substrate is oxidized or reduced by the enzyme, and a reactant such as hydrogen peroxide is correspondingly produced. The produced reactant permeates through the second selectively permeable film 36 to be supplied to the electrode 37. In the electrode 37, electrons are transferred between the reactant and the anode 38 or the cathode 39 by the voltage applied by the power supply 31. At the time, the transfer of the electrons to and from the anode 38 or the cathode 39 generates a current flow between the anode 38 and the cathode 39, and the current generated then (output for measurement) is measured by the current value measuring unit 32.

To monitor the sensitivity of the enzyme electrode 30 using the reference solution, the reference solution of the reference solution tank 21' is supplied to the flow cell 33 with the voltage being applied to the electrode 37 by the power supply 31, and a current generated then (output for correction) is measured by the current measuring unit 32.

FIG. 4 illustrates the outputs from the enzyme electrode 30 when one cycle of processing steps including washing, substrate detection, washing and sensitivity monitoring, is repeatedly performed. In FIG. 4, the outputs for two cycles are illustrated.

The calculating unit 5 calculates a substrate concentration using the output for correction in the enzyme electrode 30 when the reference solution is supplied to the flow cell in addition to the output for measurement in the enzyme electrode 30 when the specimen is supplied to the flow cell 33.

More specifically, the calculating unit 5 samples, in the same cycle, a current value (base output Rb) when a predetermined amount of time passed after the wash started (T1), a current value (output for measurement Rs) when a predetermined amount of time passed after the supply of the specimen to the flow cell 33 started (T2), and a current value (output for correction Rm) when a predetermined amount of time passed after the supply of the reference solution. The calculating unit 5 further calculates a monitored reaction value $\Delta Rm$ by subtracting the base output Rb from the output for correction Rm. The sensitivity of the enzyme electrode 30 is reflected on the monitored reaction value $\Delta Rm$. Moreover, the calculating unit 5 calculates a substrate reaction value $\Delta Rs$ by subtracting the base output Rb from the output for measurement Rs, and calculates the substrate concentration using the monitored reaction value $\Delta Rm$. To calculate the substrate concentration, for example, the substrate reaction value $\Delta Rs$ is multiplied by a modulus corresponding to the monitored reaction value $\Delta Rm$ so that a corrected reaction value is calculated, and the corrected reaction value is allocated to a given analytical curve or table. The substrate concentration may be calculated such that the substrate concentration is primarily calculated based on the substrate reaction value $\Delta Rs$, and a result of the primary calculation is corrected by the corrected reaction value.

In the substrate concentration measuring device 1, the sensitivity of the enzyme electrode 30 is monitored (output for correction Rm is measured) by means of the reference solution in order to measure each substrate, and a monitoring result thereby obtained is reflected on the calculation of the substrate concentration. Therefore, the substrate concentration measuring device 1 can suitably calculate the substrate concentration depending on the sensitivity of the enzyme electrode 30 whatever the factors are that cause the sensitivity of the enzyme electrode 30 to be variable, which is different to the conventional calibration performed, for example, at the startup of a device, at certain time intervals, or per a certain number of measurements. As a result, the substrate concentration measuring device 1 can improve a measurement accuracy and reliability.

In the substrate concentration measuring device 1 described so far, the sensitivity is monitored once to measure one substrate. The sensitivity may be likewise monitored once for a plurality of substrates in any environment where the base output Rb is stabilized.

Figure 5:
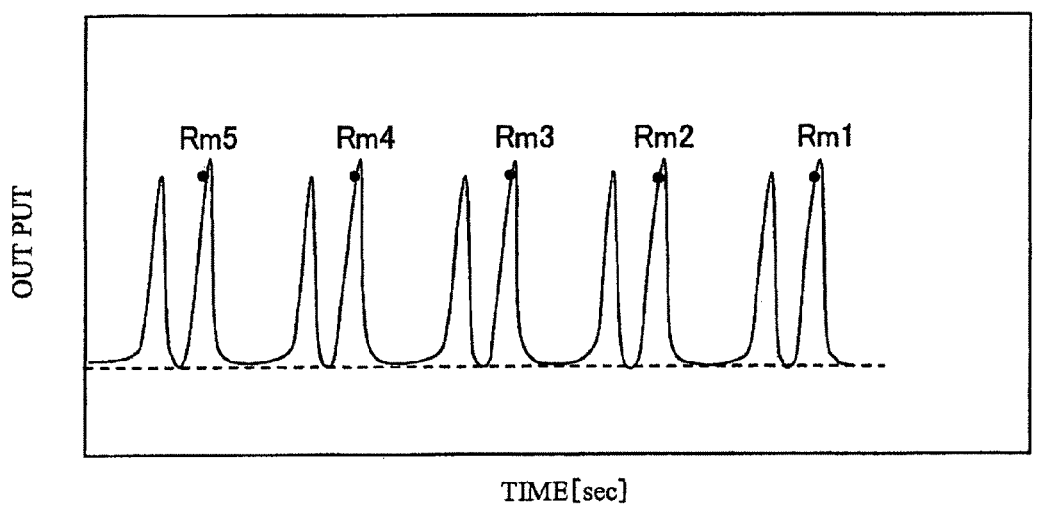
FIG. 5 is a timing chart of outputs from the enzyme electrode provided to describe another example of the operation in the calculating section.

Next, another example of the substrate concentration measuring method carried out by the calculating unit 5 is described referring to FIG. 5.

The calculating unit 5 may be configured to calculate the substrate concentration using, in addition to an output for correction Rm1 measured for the substrate to be measured, outputs for correction Rm2 to Rm5 of the substrates previously measured. More specifically, the calculating unit 5 may be configured to calculate the substrate concentration based on a mean value obtained from the output for correction Rm1 measured for the substrate to be measured and the outputs for correction Rm2 to Rm5 of the substrates previously measured.

Thus configured, any impact of the variability generated in the measurement of the output for correction is controlled by taking the mean value of the current output for correction and the outputs for correction measured in the past. As a result, a measurement reproducibility can be improved.

The number of the outputs for correction measured in the past plus the current output for correction to obtain the mean value is not limited to five as far as at least two outputs for correction can be used.

Figure 6:
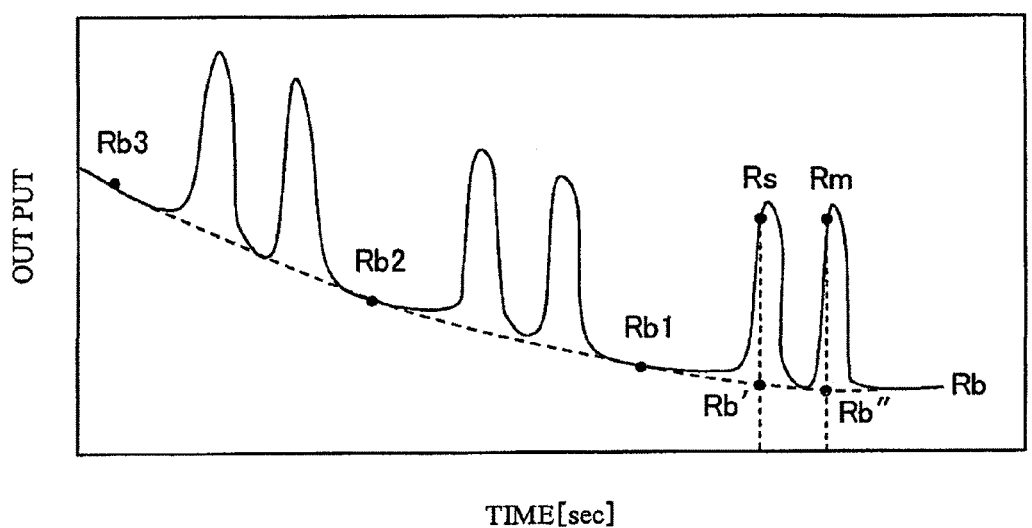
FIG. 6 a timing chart of outputs from the enzyme electrode provided to describe still another example of the operation in the calculating section.
Figure 7A:
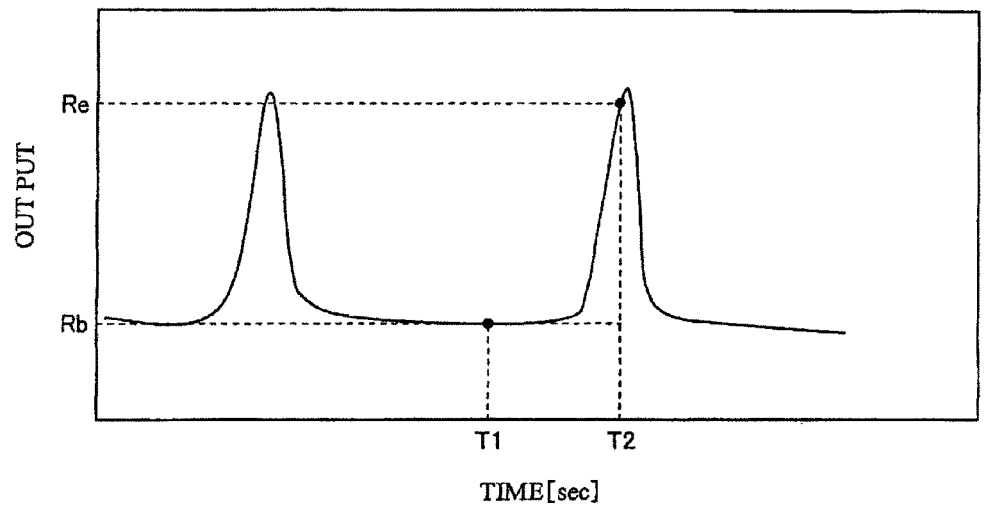
FIGS. 7A and 7B are timing charts of outputs from an enzyme electrode provided to describe a conventional substrate concentration calculating method.
Figure 7B:
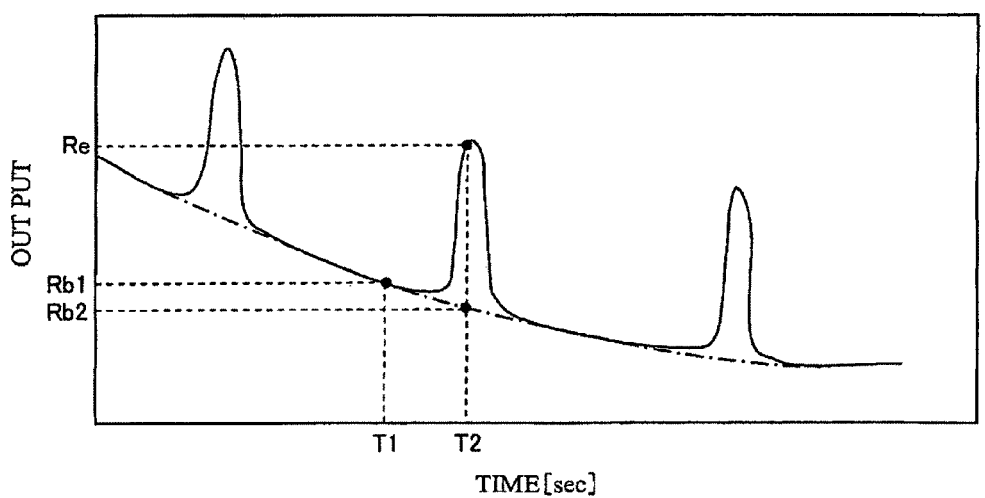

Next, still another example of the substrate concentration measuring method carried out by the calculating unit 5 is described referring to FIG. 6.

The calculating unit 5 may be configured to compare a base output Rb1 measured for the substrate to be measured to base outputs Rb2 and Rb3 of the substrates previously measured and calculate the substrate concentration based on a comparison result thereby obtained. More specifically, the calculating unit 5 determines that the base output Rb undergoes a large variation, that is, the sensitivity of the enzyme electrode 30 undergoes a large variation, in a case where the current base output Rb1 is smaller than the past base outputs Rb2 and Rb3 by a given value, and estimates base outputs Rb' and Rb" obtained by sampling the output for measurement Rs and the output for correction Rm in accordance with the time-dependent variation of the base outputs Rb1 to Rb3. Then, the calculating unit 5 calculates the substrate concentration based on the output for measurement Rs, output for correction Rm and estimated base outputs Rb' and Rb".

According to the configuration, the substrate concentration can be measured with a high accuracy even if the sensitivity of the enzyme electrode 30 degrades to a relatively large extent which typically happens immediately after the enzyme electrode 30 is replaced. When the enzyme electrode 30 is replaced, it is unnecessary to wait for the sensitivity of the enzyme electrode 30 to be stabilized before the substrate concentration is measured, which is different to the conventional calibration.

The present invention is not limited to the embodiment described so far, and can be variously modified. For example, the enzyme electrode may be configured to be fixated in the preparation tank, and the substrate concentration may be measured according to the batch system, and further, the preparation tank is omitted, and a configuration may be given such that the reagent of the reagent bottle 21 is continuously supplied to the enzyme electrode 30, and the analyte and specimen are injected from an injection valve.

What is claimed is:

1. A substrate concentration measuring method for measuring a concentration of a substrate included in a specimen based on an output for measurement from an enzyme electrode when the enzyme electrode and the substrate are reacted with each other, the method comprising the following cycle:
   (i) a first washing of the enzyme electrode;
   (ii) a reaction of the enzyme electrode with the substrate in the specimen;
   (iii) a second washing of the enzyme electrode; and
   (iv) a reaction of the enzyme electrode with a reference solution whose substrate concentration is known,
   and the method further comprising:
   measuring a base output Rb measured when the first washing or the second washing of the enzyme electrode is completed;
   measuring an output for measurement Rs of the reaction of the enzyme electrode with the substrate in the specimen;
   measuring an output for correction Rm of the reaction of the enzyme electrode with the reference solution whose substrate concentration is known;
   calculating a difference $\Delta Rm$ by subtracting Rb from Rm;
   calculating a difference $\Delta Rs$ by subtracting Rb from Rs; and calculating the substrate concentration by correcting ΔRs by ΔRm.

2. The substrate concentration measuring method according to claim 1, the method further comprising repeating the cycle for a plurality of specimens and calculating the substrate concentration for each of the plurality of specimens.

3. The substrate concentration measuring method according to claim 2, wherein the base output to be subtracted from the output for measurement to obtain the difference is estimated based on an estimation curve drawn so as to correspond to a time-dependent variation of a plurality of base outputs of the plurality of the specimens when a change that is equal to or greater than a given value is detected between the plurality of base outputs.

4. The substrate concentration measuring method according to claim 1, wherein the substrate concentration is calculated by using an output for correction for the specimen to be measured and an output for correction corresponding to at least one other specimen measured prior to measuring the output for correction for the specimen to be measured.

5. The substrate concentration measuring method according to claim 4, wherein the substrate concentration is calculated by using a mean value of the output for correction for the specimen to be measured and the output for correction corresponding to the at least one other specimen measured prior to measuring the output for correction for the specimen to be measured.

6. A substrate concentration measuring device comprising a calculating unit for calculating a concentration of a substrate included in a specimen based on an output for measurement from an enzyme electrode when the enzyme electrode and the substrate are reacted with each other, wherein the calculating unit is configured to calculate the substrate concentration in a cycle comprising:
  (i) a first washing of the enzyme electrode;
  (ii) a reaction of the enzyme electrode with the substrate in the specimen;
  (iii) a second washing of the enzyme electrode; and
  (iv) a reaction of the enzyme electrode with a reference solution whose substrate concentration is known,
  by using a base output Rb measured when the first washing or the second washing of the enzyme electrode is completed, an output for measurement Rs of the reaction of the enzyme electrode with the substrate in the specimen, and an output for correction Rm of the reaction of the enzyme electrode with the reference solution whose substrate concentration is known, and by
  calculating a difference ΔRm by subtracting Rb from Rm, calculating a difference ΔRs by subtracting Rb from Rs, and
  calculating the substrate concentration by correcting ΔRs by ΔRm.

7. The substrate concentration measuring device according to claim 6, wherein the calculating unit is configured to calculate the substrate concentration in the cycle with respect to a plurality of specimens, by using the outputs for correction measured with respect to each of the plurality of specimens.

8. The substrate concentration measuring device according to claim 7, wherein the calculating unit is configured to calculate the substrate concentration after estimating the base output to be subtracted from the output for measurement to obtain the difference based on an estimation curve drawn so as to correspond to a time-dependent variation of a plurality of base outputs of the plurality of the specimens when a change that is equal to or greater than a given value is detected between the plurality of base outputs.

9. The substrate concentration measuring device according to claim 6, wherein the calculating unit is configured to calculate the substrate concentration by using an output for correction for the specimen to be measured and an output for correction corresponding to at least one other specimen measured prior to measuring the output for correction for the specimen to be measured.

10. The substrate concentration measuring device according to claim 9, wherein the calculating unit is configured to calculate the substrate concentration by using a mean value of the output for correction for the specimen to be measured and the output for correction corresponding to the at least one other specimen measured prior to measuring the output for correction for the specimen to be measured.

11. The substrate concentration measuring device according to claim 6, further comprising:
  a specimen preparing unit for preparing a specimen to be reacted with the enzyme electrode;
  a reference solution retaining tank for retaining the reference solution for obtaining the output for correction; and
  a selecting unit for selecting one of a state where the specimen is to be supplied, or a state where the reference solution is to be supplied, to the enzyme electrode.

* * * * *